(12) United States Patent
Pokorney

(10) Patent No.: US 7,022,112 B2
(45) Date of Patent: Apr. 4, 2006

(54) HIGH PRESSURE SYRINGE

(76) Inventor: James L. Pokorney, 303 Washington St., Northfield, MN (US) 55057

( * ) Notice: Subject to any disclaimer, the term of this patent is extended or adjusted under 35 U.S.C. 154(b) by 323 days.

(21) Appl. No.: 10/034,686

(22) Filed: Dec. 27, 2001

(65) Prior Publication Data
US 2002/0087125 A1    Jul. 4, 2002

Related U.S. Application Data

(63) Continuation of application No. 09/045,441, filed on Mar. 20, 1998.

(60) Provisional application No. 60/041,558, filed on Mar. 21, 1997.

(51) Int. Cl.
A61M 5/315    (2006.01)

(52) U.S. Cl. .................................................... 604/227
(58) Field of Classification Search ............ 604/93.01, 604/181, 187, 218, 220, 221, 227
See application file for complete search history.

(56) References Cited

U.S. PATENT DOCUMENTS

| 201,443 | A | | 3/1878 | Parker |
| 794,190 | A | * | 7/1905 | Schneyder ................. 604/227 |
| 822,079 | A | | 5/1906 | Roussy |
| 1,325,699 | A | * | 12/1919 | Osterhaus ................... 604/59 |
| 1,549,006 | A | | 5/1925 | Kazmousky |
| 1,654,905 | A | | 1/1928 | Voos |
| 2,420,102 | A | | 5/1947 | Shuford |
| 2,632,445 | A | | 3/1953 | Kas, Sr. |
| 2,671,449 | A | | 3/1954 | Dann |
| 2,882,901 | A | | 4/1959 | Venezia |
| 3,043,304 | A | | 7/1962 | Higgins |
| 3,118,447 | A | | 1/1964 | Hunt et al. |
| D202,754 | S | | 11/1965 | Naftolin et al. |
| 3,306,290 | A | | 2/1967 | Weltman |
| 3,388,941 | A | | 1/1968 | Marcus |
| 3,487,834 | A | | 1/1970 | Smith, Jr. et al. |
| 3,758,006 | A | * | 9/1973 | Gravelee ................... 222/323 |
| 4,263,911 | A | | 4/1981 | McCormack et al. |
| 4,340,051 | A | | 7/1982 | Leibinsohn |
| D289,434 | S | | 4/1987 | Morrison et al. |
| D303,010 | S | | 8/1989 | Jabbusch |
| 4,925,449 | A | | 5/1990 | Saez et al. |
| 4,929,238 | A | * | 5/1990 | Baum ......................... 604/208 |
| D320,276 | S | | 9/1991 | Baum |
| D325,437 | S | | 4/1992 | Hull |

(Continued)

OTHER PUBLICATIONS

Merit Medical Systems, Inc. Brochure, "CCS The Control Syringe That's an Absolute Wonder", 1990.

(Continued)

*Primary Examiner*—LoAn H. Thanh
(74) *Attorney, Agent, or Firm*—Fredrikson & Byron, P.A.

(57) ABSTRACT

A hand-operated syringe for injecting a liquid under high pressure. The syringe has an elongated barrel with proximal and distal ends, the barrel having opposing finger grips at its proximal end with each finger grip having a proximal inner portion defining a most proximal pressure point closely adjacent the barrel, the pressure points defining a plane substantially perpendicular to the barrel's axis. A plunger is received in the barrel and has a proximal end that includes a pressure surface adapted to receive manual pressure. The pressure surface of the plunger and the finger pressure points are arranged so that when the plunger is in its fully inserted position, its pressure surface is spaced distally of the plane defined by the finger pressure points.

14 Claims, 4 Drawing Sheets

U.S. PATENT DOCUMENTS

| | | |
|---|---|---|
| 5,215,536 A | 6/1993 | Lampropoulos et al. |
| 5,221,348 A | 6/1993 | Masano |
| 5,226,897 A | 7/1993 | Nevens et al. |
| 5,246,011 A | 9/1993 | Caillouette |
| 5,395,379 A | 3/1995 | Deutchman et al. |
| 5,460,617 A | 10/1995 | Minkus et al. |
| 5,554,132 A | 9/1996 | Straits et al. |
| 5,651,372 A | 7/1997 | Caillouette |

OTHER PUBLICATIONS

NAMIC Angiographic Systems Division Brochure "NAMIC 10cc Angiographic Syringe", Jan. 1988.

International Standard ISO Brochure "Sterile Hypodermic Syringes for Single Use, Part 1: Syringes for Manual Use" Reference number ISO 7886-1, (1993) pp. 2, 5.

B-D Product Catalog 1993, Becton-Dickinson, pp. A1-A4.

\* cited by examiner

HIGH PRESSURE SYRINGE

This application claims priority from provisional patent application U.S. Ser. No. 60/041,558, filed Mar. 21, 1997 and is a continuation of application Ser. No. 09/045,441, filed Mar. 20, 1998, now abandoned.

FIELD OF THE INVENTION

The present invention generally relates to syringes, and more particularly to high pressure control syringes.

BACKGROUND OF THE INVENTION

High pressure syringes have been used in medical procedures for many years. To facilitate single hand retraction and injection motions, a high pressure syringe is typically designed with thumb and hand rings or grips to allow sufficient hand control in both the injection (depression of plunger) and the aspiration (retraction of plunger) modes.

Injection of radiopaque dye solutions into the human body during diagnostic and therapeutic cardiovascular procedures is one application which would employ a high pressure syringe. These procedures are conducted millions of times each year. The purpose of the procedure is to momentarily displace blood with the radiopaque dye so that the details of the fluid filled vessels may be captured by radioimaging on film or screen.

Generally, radioimaging is done more frequently and elaborately during diagnostic procedures, where mapping of the anatomy is required for further evaluations. But dye injection is also needed during therapeutic procedures, such as angioplasty, in order to enable the physician to evaluate catheter location, condition of the lesion, nature of the stenosis, progress of the procedure, effectiveness of the dilatation, and location and orientation of stent placement, if necessary.

During an angiography or angioplasty procedure, the interventionalist uses a hand-held syringe to inject a sufficient volume and flow rate of radiopaque dye to opacify the artery under study. Inadequately opacified vessels generally result in overestimation of stenosis severity due to contrast "streaming" as it forms a layer with unopacified blood. The specific volume and rate of injection is controlled by the interventionalist by observing the fluoroscopic image. For instance, in the right coronary artery, 3–6 cm$^3$ of contrast are injected at a rate of 2–3 cm$^3$ per second, and in the left coronary artery, 4–7 cm$^3$ are injected at the same rate.

To generate this critical volume/flow dynamic through a narrow catheter lumen using viscous radiopaque dye, syringe pressures of 100 psi or more are often required. Such high pressure delivery is critical to create the appropriate contrast filling. If the dye is delivered with insufficient injection pressures, inadequately opacified vessels can result causing either incorrect fluoroscopic images or repeat injections. Repeating the injection subjects the patient to a higher risk of adverse side effects of the radiopaque dye and also increases the cost of the procedure. A major reason for inadequate injection volumes is the limitations on current syringes to deliver the necessary pressure, especially with users who do not possess above average hand strength.

In the past, the focus in newly designed syringes was on increasing injection pressure by increasing a user's ability to generate greater hand forces. Finger and hand grips have been made as ergonomically comfortable as possible to allow muscle leverage to generate maximum hand squeezing forces. Designs such as U.S. Pat. No. 4,925,449 (hereinafter "'449") and U.S. Pat. No. 5,554,132 have focused on improving the hand grips to achieve maximum gripping power. The '449 patent disclosed a shortened syringe plunger stroke to allow the plunger to fit within the operator's palm in an attempt to maximize the force that the hand could exert.

In addition, U.S. design Pat. Des. No. 289,434, U.S. Pat. No. Des. 320,276, and U.S. Pat. No. Des. 325,437 show high pressure syringe designs which emphasize ergonomically designed finger and thumb grips. None of these designs attempt to solve the basic problem of high force/high volume requirements inherent in the procedure. As a result, there is a clear need for an fresh approach to this problem.

It is well known that syringe injection pressure is calculated as the ratio of hand force to plunger cross section area.

Syringe Pressure=Hand Force/Plunger Area (or barrel internal cross-section area)

One commercially available high pressure syringe (Merit Medical, model CCS460) provides increased injection pressure by reducing the barrel cross-sectional area. However, due to the traditional design of the syringe, this decrease in the barrel's cross-sectional area requires a reduction in syringe volume from 10 cubic centimeters to 6 cubic centimeters to maintain a plunger stroke length that is ergonomically acceptable. This lower volume is undesirable in most interventional procedures.

It is also well known that small diameter tuberculin syringes with an injection volume of about 1 cubic centimeter can generate substantial injection pressures. But again, the small injection volume is inadequate for many procedures requiring high pressure injections.

Neither ergonomic refinements or reduced syringe barrel cross-sectional areas have provided a device which delivers the pressures and volumes necessary for the medical uses described above, while reducing the amount of force needed from the syringe user.

To provide high delivery pressures while reducing the force provided by the user, one must reduce the barrel's cross-sectional area. To maintain the needed delivery volume, one must increase the stroke length. However, existing syringe design has already reached the maximum stroke length usable by the average hand. In the present invention, a unique syringe design allows an increased stroke length within the ergonomic limitations of the average hand in conjunction with a lowered barrel cross-sectional area, thereby reducing the force required from the user without reducing delivery pressure or volume.

SUMMARY OF THE INVENTION

One embodiment of the present invention is a hand operated syringe for injecting a liquid which includes an elongated barrel having proximal and distal ends and an exit orifice at its distal end. A pair of opposing finger grips are present at the proximal end of the barrel, each having a proximal inner portion defining a most proximal pressure point closely adjacent the barrel to which finger pressure is applied proximally during operation of the syringe, the pressure points defining a plane substantially perpendicular to the barrel's axis.

A plunger is received in the barrel and it has a proximal end protruding from the barrel, the proximal end including a pressure surface adapted to receive manual pressure from, e.g., the thumb in an injection procedure. The plunger is movable between retracted and fully inserted positions within the barrel to discharge a volume of liquid through the exit orifice. The pressure surface of the plunger and the finger pressure points closely adjacent the barrel are arranged so that when the plunger is in its fully inserted position, its pressure surface is spaced distally of a plane defined by the finger pressure points which is substantially perpendicular to the barrel's axis. In one embodiment of the invention the plunger pressure surface lies substantially in said plane when the plunger is in its fully inserted position.

An additional embodiment of the present invention includes an elongated barrel that has proximal and distal ends and an exit orifice at its distal end. This barrel defines a fluid reservoir that has a cross-sectional area A. A pair of opposing finger grips are present at the proximal end of the barrel, each having a proximal inner portion defining a distally-facing pressure point to which finger pressure is applied proximally during operation of the syringe. These points lay in a plane substantially perpendicular to the barrel's axis.

A plunger is received in the barrel and has a proximal end protruding from the barrel, the proximal end including a proximally-facing pressure surface adapted to receive manual pressure. The plunger is movable through a stroke length S between retracted and fully inserted positions within the barrel to discharge a volume V of fluid through the its exit orifice. When the plunger is in its fully inserted position, its pressure surface is spaced distally of the plane by a distance L, where L is greater than or equal to 0.01 S and preferably greater than or equal to 0.02 S.

DESCRIPTION OF THE DRAWING(S)

DETAILED DESCRIPTION OF THE PREFERRED EMBODIMENT

Figure 1:
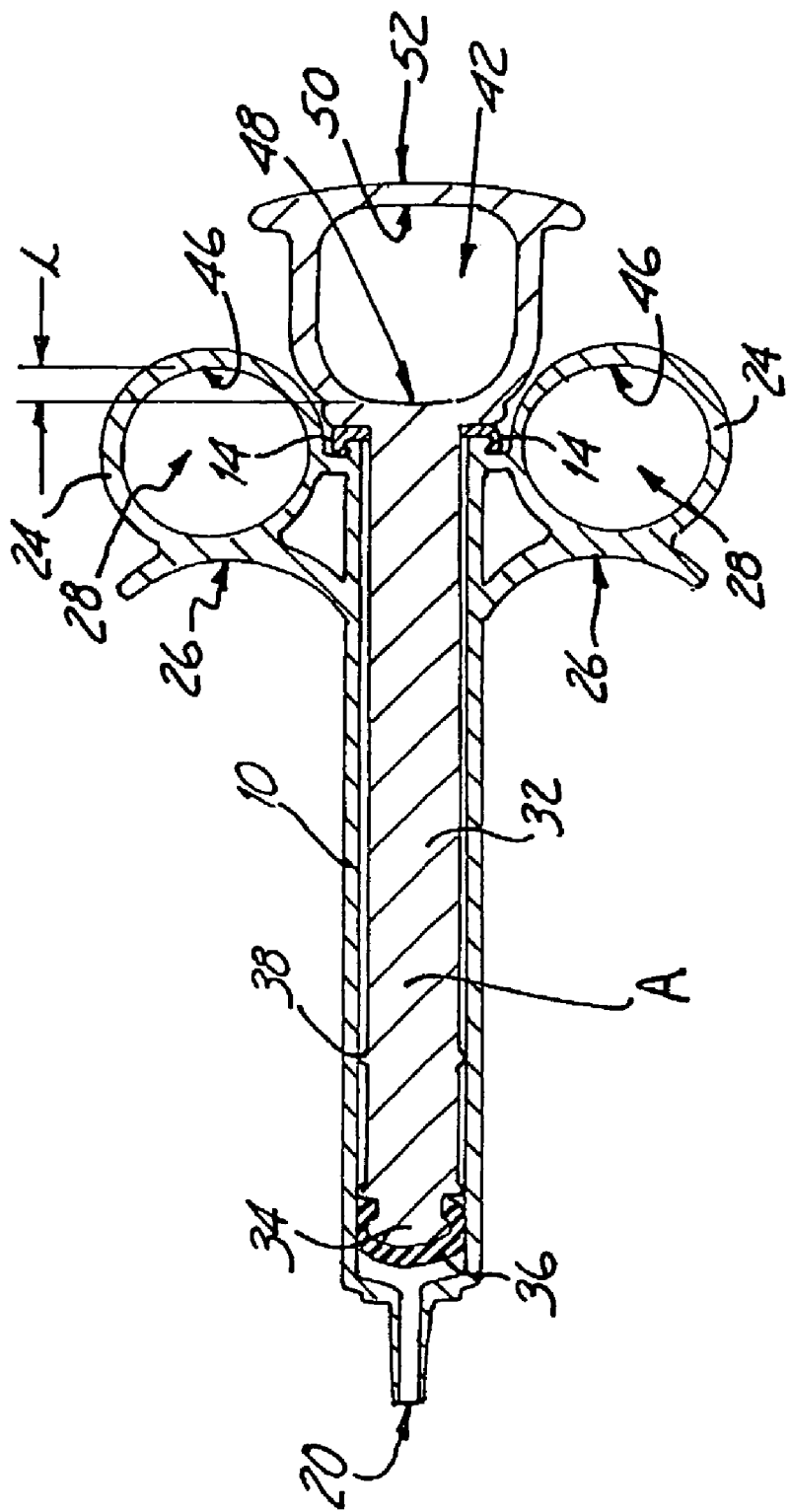
FIG. 1 is a cross-sectional view of one embodiment of the invention showing its plunger fully depressed.
Figure 2:
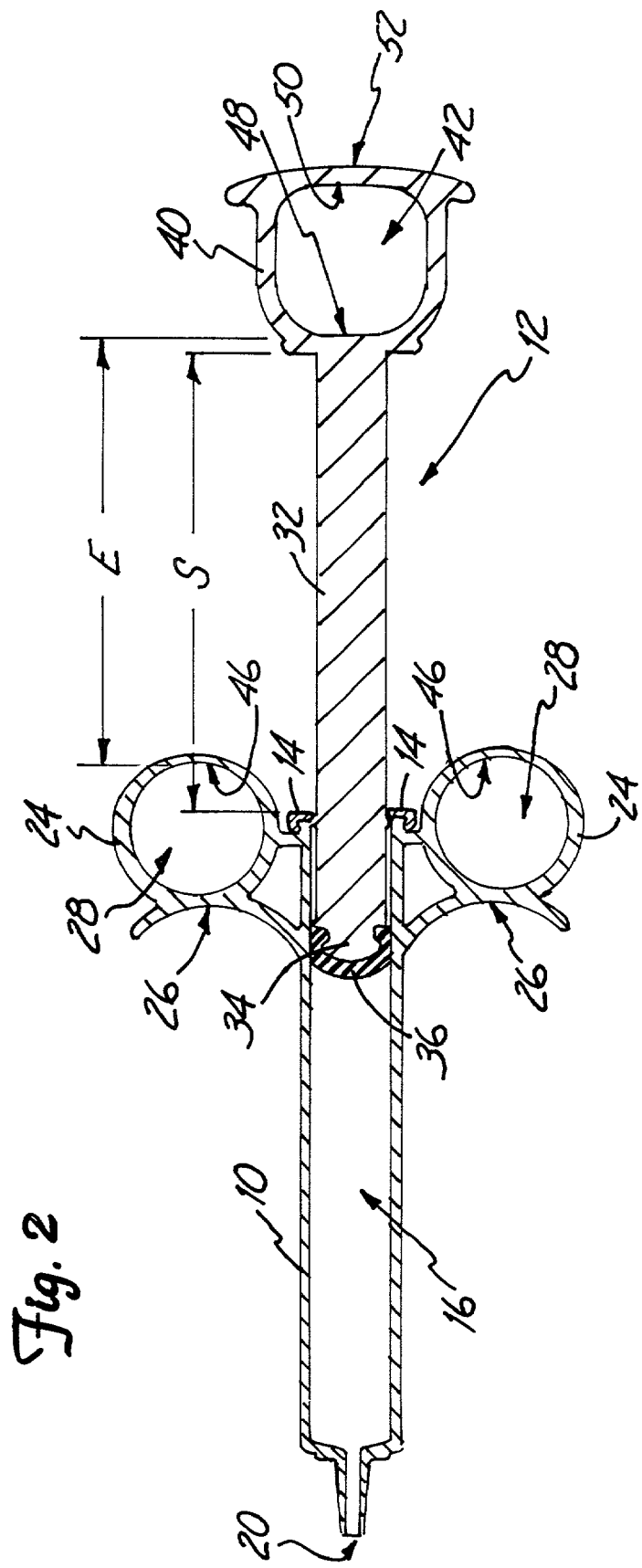
FIG. 2 is a cross-sectional view of the embodiment of FIG. 1 with its plunger retracted.

As shown in FIGS. 1 and 2, one embodiment of the present invention includes a barrel body 10, plunger 12, and retaining ring 14.

In this embodiment, barrel body 10 is composed of a rigid clear polymer such as polycarbonate. This body 10 defines an internal lumen or reservoir 16 adapted to hold the fluid to be injected. At the distal end of the body 10 is a nozzle or exit orifice 20. Generally this orifice has a smaller diameter than the body 10, and is used to connect the syringe to extension tubing, catheter fittings, needles, and the like.

At the proximal end of body 10 opposite the orifice 20, body 10 has an opening designed to accept a plunger 12.

In addition, at or adjacent the more proximal end of body 10 are a pair of opposing finger grips 24. These finger grips may be integrally formed with the syringe body 20 or otherwise attached. In a preferred embodiment these finger grips 24 are shaped to accommodate the comfortable gripping of the body 10 by the first and second (index and middle) fingers of the user's hand.

In one embodiment these grips 24 will define an opening 28 for the insertion of fingers. Within these openings 28, to the proximal side of the grips 26, are distally-facing pressure points 46 to which finger pressure is applied proximally during the operation of the syringe. Finger grips 24 are so positioned that the pressure points 46 extend proximally beyond the most proximal end of the body 10.

An additional embodiment of the invention provides additional ergonomic efficiencies by locating the finger pressure points as close to the barrel as possible while still allowing the plunger pressure surface to advance beyond the finger pressure points. The pressure points 46 are closely adjacent to barrel 10. If finger grips adapted to allow more than one finger to simultaneously contact each grip are provided, the pressure points of the fingers closest to the barrel are the most closely adjacent pressure points.

If desired, additional finger grips 24 may be provided to afford substantially curved portions to the distal side of the finger grip 24, which may serve as an alternate gripping position 26.

A plunger 12, composed of a rigid polymer such as ABS (acrylonitrile-butadiene-styrene), is provided to control the aspiration and evacuation of the fluids delivered by the syringe. This plunger 12 consists of a shaft 32 having a distal end 34. In a preferred embodiment a resilient seal 36 is placed at the distal end 34 of shaft 32. This resilient seal 36 helps provide an adequate vacuum for the aspiration of fluids into the body 10 as well as assisting in the complete evacuation of the same. The seal 36 can be made of a number of materials including an elastic polymer such as polyisoprene. For some particularized applications it may be important to select a material for this seal which is chemically or biologically compatible with the fluids being dispensed by the syringe. In one embodiment the shaft 34 is spined to increase its column strength while providing a corresponding decrease in weight.

Near the distal end of shaft 32 an annular ridge 38 is provided. This ridge 38 provides for the retention of the plunger 12 within the body 10 when used in conjunction with retaining ring 14.

The proximal end of plunger 12 is adapted to receive manual pressure. In one embodiment this adaptation is in the form of a thumb ring 40. This ring 40 defines an opening 42 for the insertion of a thumb. The distal inside portion of ring 40 includes a pressure surface 48 where thumb pressure is applied during operation of the syringe. While it is possible to provide such a pressure surface without a ring structure, it is desirable to have both the distal pressure surface 48 and also a proximal pressure surface 50, where surface 50 serves to facilitate retraction of the plunger during the aspiration portion of its use. As desired, the thumb ring may include an external, proximally facing surface 52 to facilitate the application of pressure by the hand palm.

In order to encourage the retention of plunger 12 within body 10, a retaining ring 14 is placed on the proximal end of body 10. In one embodiment this retaining ring 14 is made of an elastic polymer such as polypropylene, and is attached by snap fitting or bonding to body 10. This elastic retaining ring 46 has an inside diameter slightly smaller than the outside diameter of the plunger's annular ridge 38, thereby providing resistance to the removal of plunger 12 from body 10. However, the elastic nature of the ring 14 allows the plunger to "snap" into the barrel body 10 by exerting sufficient force to overcome the resistance provided by the elastic ring 14.

Once assembled, plunger 12, and more specifically seal 36, fit snugly within the lumen 16 to allow for the aspiration and evacuation of fluid during the operation of the syringe.

As described, this syringe design significantly reduces the hand force necessary to generate high pressure injections without decreasing the injection volume V by reducing the barrel's cross-sectional area A while simultaneously increasing the plunger stroke length S to maintain the same injectate volume. This is achieved by positioning the finger grips 24 to allow the thumb to advance past the fingers at full plunger advancement. By doing this, the overall stroke length S is increased without requiring further hand extension. If desired, the thickness of the retainer ring may also be minimized.

Figure 3:
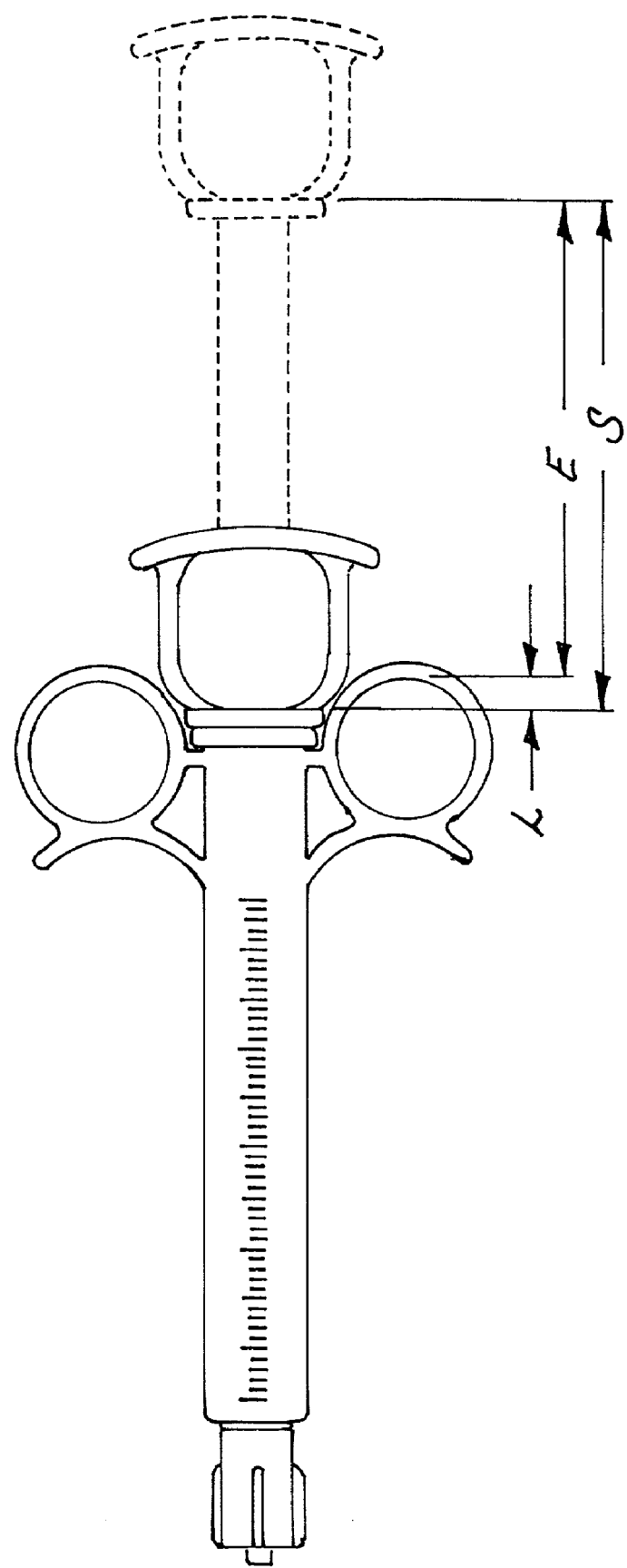
FIG. 3 is a side view of one embodiment of the invention showing the plunger in both its retracted (phantom line) and fully inserted positions.
Figure 4:
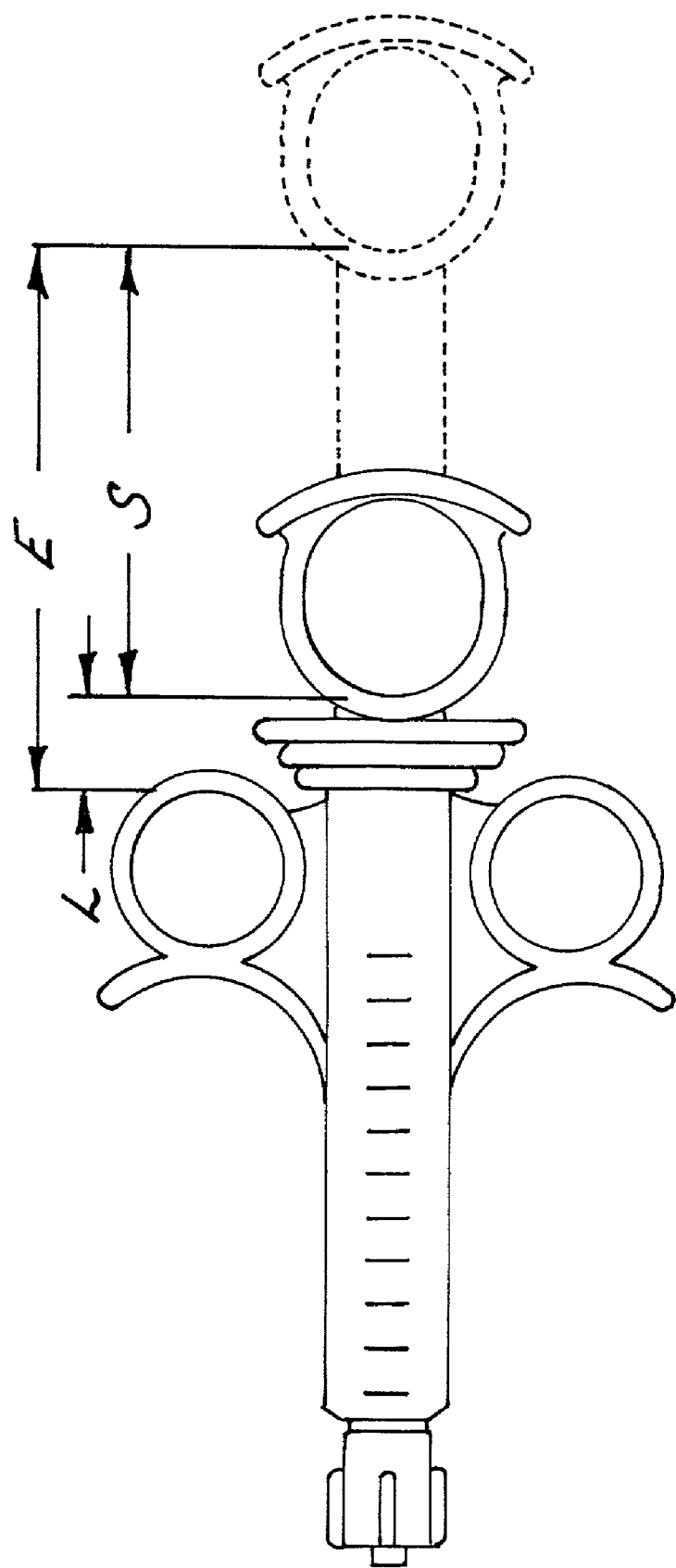
FIG. 4 is a side view of a commercially available syringe showing the plunger in both its retracted and fully inserted positions.

Table 1 compares the invention, as shown in FIG. 3, to a popular syringe manufactured by NAMIC, Inc. (Glen Falls, N.Y. Catalog No. 70085003) as shown in FIG. 4.

TABLE 1

| Design | Injectate Volume (V) | Barrel Cross-sectional Area (A) | Plunger Stroke (S) | Hand Extension at Full Retraction (E) | Hand Extension at Full Advancement (L) | Hand Force Required to Generate 100 psi Injection Pressure |
|---|---|---|---|---|---|---|
| invention | 10 cm$^3$ | 0.19 in.$^2$ | 3.2 in. | 3.0 in. | 0.2 in. | 19 lbs. |
| NAMIC | 10 cm$^3$ | 0.26 in.$^2$ | 2.4 in. | 3.0 in. | −0.6 in. | 26 lbs. |

Plunger stroke S at full retraction is substantially lengthened in this invention, from 2.4 inches to 3.2 inches without lengthening the full hand extension E distance of 3.0 inches common to both designs. Hand extension at full advancement L is defined as the distance measured distally from a plane substantially perpendicular to the barrel's axis defined by the most proximal pressure points 46 to the position assumed by the plunger pressure surface 48 when the plunger is fully inserted. The distance L in a preferred embodiment is about 0.2 inches. In the table above, the negative value for L in the NAMIC example indicates that its pressure surface 48 lies on the proximal side of the plane.

By maximizing stroke lengths S, the barrel 10 cross-sectional area A can be substantially reduced without decreasing volume V.

In the design example shown in Table 1, the barrel cross-sectional area A is reduced from 0.26 square inches to 0.19 square inches and the force required to generate 100 psi injection pressure is reduced from 26 pounds to 19 pounds.

Assuming a maximum hand force of 30 pounds, and a maximum hand extension is extension is 3.0 inches, to generate a high pressure injection 100 psi the barrel 10 cross-sectional area must be no larger than 0.3 square inches. The volume of liquid discharged may range from about 3$^{cm3}$ to about 20$^{cm3}$, and more desirably from about 5$^{cm3}$ to about 10$^{cm3}$.

While a preferred embodiment of the present invention has been described, it should be understood that various changes, adaptations and modifications may be made therein without departing from the spirit of the invention and the scope of the appended claims. This includes a high pressure syringe adapted for use in non-medical fields such as the manual application of viscous adhesives.

What is claimed is:

1. A hand operated syringe for injecting a liquid, comprising:
    a) an elongated barrel having proximal and distal ends and an exit orifice at its distal end;
    b) a pair of opposing finger grips for reception of the index and middle fingers, respectively, of a user's hand and carried at the proximal end of the barrel, each grip having a generally distally facing gripping surface having an arcuate portion nearer the barrel than any other arcuate gripping surface portion and defining a most proximal point on said arcuate gripping surface to which finger pressure is applied proximally during operation of the syringe, said points defining a plane substantially perpendicular to the barrel's axis;
    c) a plunger received in the barrel and having a proximal end protruding from the barrel, said proximal end including a pressure surface adapted to receive manual pressure; the plunger being movable between retracted and fully inserted positions within the barrel to discharge a volume of liquid through the exit orifice, the pressure surface of the plunger and the finger pressure points closely adjacent the barrel being so arranged that when the plunger is in its fully inserted position, its pressure surface is spaced distally of said plane.

2. The syringe of claim 1 wherein the volume is from about 3 cm$^3$ to about 20 cm$^3$.

3. The syringe of claim 1 wherein the volume is from about 5 cm$^3$ to about 10 cm$^3$.

4. A hand operated syringe for injecting a liquid, comprising:
    a) an elongated barrel having proximal and distal ends and an exit orifice at its distal end, the elongated barrel having a substantially constant diameter;
    b) a pair of opposing finger grips for reception of the index and middle fingers, respectively, of a user's hand and spaced apart at least the diameter of the barrel and carried at the proximal end of the barrel, each grip having a generally distally facing gripping surface having an arcuate portion nearer the barrel than any other arcuate gripping surface portion and defining a finger pressure point to which finger pressure is applied proximally during operation of the syringe, said points defining a plane substantially perpendicular to the barrel's axis;
    c) a plunger received in the barrel and having a proximal end protruding from the barrel, said proximal end including a pressure surface adapted to receive manual pressure; the plunger being movable between retracted and fully inserted positions within the barrel to discharge a volume of liquid through the exit orifice, the pressure surface of the plunger and the finger pressure points closely adjacent the barrel being so arranged that when the plunger is in its fully inserted position, its pressure surface is spaced distally of said plane.

5. The syringe of claim 1 wherein said discharge volume is from about 3 cm$^3$ to about 20 cm$^3$.

6. The syringe of claim 1 wherein said discharge volume is from about 5 cm$^3$ to about 10 cm$^3$.

7. The syringe of claim 1 wherein said barrel defines a fluid reservoir having a cross-sectional area A wherein area A is less than 0.3 square inches.

8. The syringe of claim 7 wherein area A is about 0.2 square inches.

9. They syringe of claim 1 wherein said plunger is movable through a stroke length S between retracted and fully inserted positions within the barrel, and wherein, when the plunger is in its fully inserted position, its pressure surface is spaced distally of said plane by a distance L that is greater than or equal to about 0.02 S.

10. The syringe of claim 9 wherein distance L is about 0.06 S.

11. A hand operated syringe for injecting a liquid, comprising:
   a) an elongated barrel having proximal and distal ends and an exit orifice at its distal end;
   b) a pair of opposing finger grips for reception of fingers of a user's hand and carried at the proximal end of the barrel, each finger grip having a generally distally facing gripping surface having a pressure point at its center to which finger pressure is applied proximally during operation of the syringe, said pressure points defining a plane substantially perpendicular to the barrel's axis;
   c) a plunger received in the barrel and having a proximal end protruding from the barrel, said proximal end including a pressure surface adapted to receive manual pressure; the plunger being movable between retracted and fully inserted positions within the barrel to discharge a volume of liquid through the exit orifice, the pressure surface of the plunger and the finger pressure points closely adjacent the barrel being so arranged that when the plunger is in its fully inserted position, its pressure surface is spaced distally of said plane.

12. The syringe of claim 11 wherein each of said gripping surfaces is arcuate, and wherein said pressure point is at the most proximal point of said arcuate gripping surface.

13. The syringe of claim 11 or claim 12 wherein said finger grips each are configured as circular openings sized to receive only a single finger.

14. A hand operated syringe for injecting a liquid, comprising:
   a) an elongated barrel having proximal and distal ends and an exit orifice at its distal end;
   b) a pair of opposing finger grips carried at the proximal end of the barrel and spaced apart at least the diameter of the barrel, each having a generally distally facing gripping surface against which finger pressure is applied proximally during operation of the syringe, each gripping surface having one finger pressure point that is more closely adjacent to the barrel than any other finger pressure point of said gripping surface, said more closely adjacent pressure points defining a plane substantially perpendicular to the barrel's axis,
   c) a plunger received in the barrel and having a proximal end protruding from the barrel, said proximal end including a pressure surface adapted to receive manual pressure; the plunger being movable between retracted and fully inserted positions within the barrel to discharge a volume of liquid through the exit orifice, the pressure surface of the plunger and the finger pressure points closely adjacent the barrel being so arranged that when the plunger is in its fully inserted position, its pressure surface is spaced distally of said plane.

* * * * *